United States Patent
Mosrin et al.

(10) Patent No.: US 10,766,909 B2
(45) Date of Patent: Sep. 8, 2020

(54) PROCESS FOR PREPARING HALOGENATED PYRIDINE DERIVATIVES

(71) Applicant: Bayer CropScience Aktiengesellschaft, Monheim am Rhein (DE)

(72) Inventors: Marc Mosrin, Cologne (DE); Ruediger Fischer, Pulheim (DE); Dominik Hager, Monheim (DE); Laura Hoffmeister, Duesseldorf (DE); Nina Kausch-Busies, Bergisch Gladbach (DE); David Wilcke, Duesseldorf (DE); Matthieu Willot, Duesseldorf (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/312,568

(22) PCT Filed: Jun. 28, 2017

(86) PCT No.: PCT/EP2017/065989
§ 371 (c)(1),
(2) Date: Dec. 21, 2018

(87) PCT Pub. No.: WO2018/007224
PCT Pub. Date: Jan. 11, 2018

(65) Prior Publication Data
US 2019/0330241 A1    Oct. 31, 2019

(30) Foreign Application Priority Data
Jul. 5, 2016    (EP) ...................................... 16178022

(51) Int. Cl.
*C07F 3/06* (2006.01)
*C07D 213/803* (2006.01)
*C07D 213/79* (2006.01)
*C07D 213/61* (2006.01)

(52) U.S. Cl.
CPC ...................................... *C07F 3/06* (2013.01)

(58) Field of Classification Search
None
See application file for complete search history.

(56) References Cited

U.S. PATENT DOCUMENTS

| | | | |
|---|---|---|---|
| 3,947,457 A | 3/1976 | McGregor et al. | |
| 2012/0136000 A1* | 5/2012 | Jimenez | A61P 17/06 514/252.11 |

FOREIGN PATENT DOCUMENTS

| | | |
|---|---|---|
| WO | 2012/052948 A1 | 4/2012 |
| WO | 2016/010897 A1 | 1/2016 |

OTHER PUBLICATIONS

International Search Report issued in counterpart Application No. PCT/EP2017/065989, dated Aug. 9, 2017.
Mongin et al., "Advances in the directed metallation of azines and diazines (pyridines, pyrimidines, pyrazines, pyridazines, quinolines, benzodiazines and carbolines). Part 1: Metallation of pyridines, quinolines and carbolines" Tetrahedron, (2001) vol. 57: 4059-4090.
Katia Snegaroff et al: "Deprotonative Metalation of Chloro- and Bromopyridines Using Amido-Based Bimetallic Species and Regioselectivity-Computed CH Acidity Relationships-", Chemistry A European Journal, Bd. 17, Nr. 47, Nov. 18, 2011 (Nov. 18, 2011), Seiten 13284-13297.
Dhau Jaspreet S. et al: "A study on the BF3directed lithiation of 3-chloro- and 3-bromopyridine", Tetrahedron, 8d. vol. 69, No. 48, (2013), pp. 10284-10291, XP028761490.
Khartabil et al., "Metalation of Pyridines with nBull-LI-Aminoalkoxide Mixed Aggregates: The Origin of Chemoselectivity" JACS (2010) vol. 132: 2410-2416.
Jaric, Milica et al., "Selective and Multiple Functionalization of Pyridines and Alkaloids via Mg- and Zn Organometallic Intermediates" Organic Letters (2011) vol. 13, No. 9: 2306-2309.
Haas et al., "Oxidative Homocoupling of Diheteroaryl- or Diarylmanganese Reagents Generated via Directed Manganation Using TMP2Mn" Synlett (2015), vol. 26: 1515-1519.

(Continued)

*Primary Examiner* — Zinna Northington Davis
(74) *Attorney, Agent, or Firm* — McBee Moore & Vanik, IP, LLC

(57) ABSTRACT

The present invention relates to a process for preparing halogenated pyridine derivatives of the formula (II) proceeding from compounds of the formula (I) via intermediates of the formula (IIIa) or (IIIb)

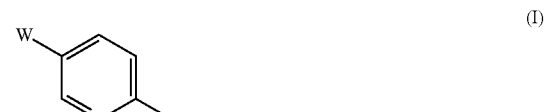

(I)

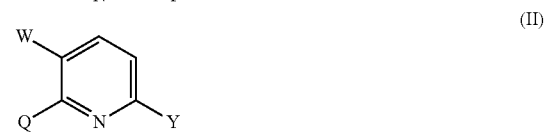

(II)

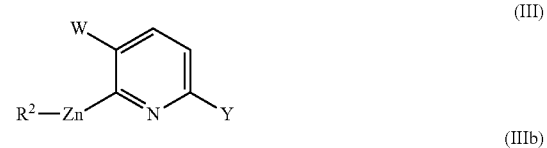

(III)

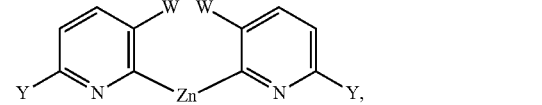

(IIIb)

where the radicals
Q and W are each independently halogen, $R^2$ is halogen or —O-pivaloyl, and Y is halogen, $CO_2R^1$ or $NO_2$, where $R^1$ is $(C_1\text{-}C_6)$-alkyl or $(C_1\text{-}C_6)$-haloalkyl.

19 Claims, No Drawings

(56) References Cited

OTHER PUBLICATIONS

Wunderlich et al., "(tmp) 2Zn-2MgCl2 2 LiCl: A Chemoselective Base for the Directed Zincation of Sensitive Arenes and Heteroarenes" Angewandte Chemie (2007) vol. 46: 7685-7688.

Mosrin et al., "TMPZnCl-LiCl: A New Active Selective Base for the Directed Zincation of Sensitive Aromatics and Heteroaromatics" Organic Letters, (2009) vol. 11, No. 8: 1837-1840.

Mosrin et al., "Regio- and Chemoselective Multiple Functionalization of Pyrimidine Derivatives by Selective Magnesiations using TMPMgCl-LiCl" Organic Letters (2008) vol. 10, No. 12: 2497-2500.

* cited by examiner

PROCESS FOR PREPARING HALOGENATED PYRIDINE DERIVATIVES

CROSS-REFERENCE TO RELATED APPLICATIONS

This application is a National Stage entry of International Application No. PCT/EP2017/065989, filed Jun. 28, 2017, which claims priority to European Patent Application No. 16178022.6, filed Jul. 5, 2016.

BACKGROUND

Field

The present invention relates to a process for preparing halogenated pyridine derivatives of the formula (II)

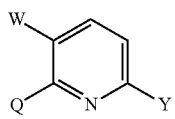

proceeding from compounds of the formula (I)

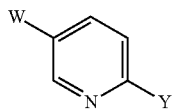

via intermediates of the formula (IIIa) or (IIIb)

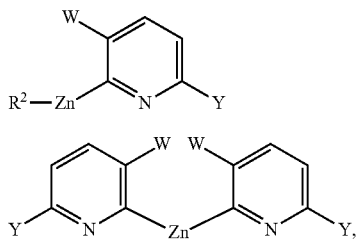

in which the structural elements shown in the formulae (I), (II), (IIIa) and (IIIb) have the definitions given below. The invention further relates to halogenated pyridine derivatives and intermediates of this kind.

Description of Related Art

Halogenated pyridine derivatives of the formula (II) are of great industrial significance for the pharmaceutical and agrochemical industry and are, for example, an important reaction partner, inter alia, in the preparation of compounds that are effective as pesticides, for example.

The literature describes the metallation of pyridines in the presence of lithium bases or magnesium bases (LDA, TMPLi, TMPMgCl.LiCl) and must be carried out at very low temperatures (−78° C. to −100° C. with lithium, −78° C. to −30° C. with magnesium), cf. for example Tetrahedron 2001 (57), p. 4059ff, Journal of the American Chemical Society 2010 (132), p. 2410ff and Organic Letters 2011 (13), p. 2306ff. The use of the complex manganese base $TMP_2Mn.2MgCl_2.4LiCl$ for the deprotonation of 2,5-bis (substituted) pyridines is also described in Synlett 2015 (26), p. 1515ff, but only to carry out oxidative homo-couplings. Metallations of some substituted pyridines at the 4 position in the presence of zinc bases are known, as described in Angewandte Chemie 2007 (46), p. 7685ff or Organic Letters 2009 (11), p. 1837ff, but not of 2,5-bis(substituted) pyridines at the 6 position.

The chemical synthesis methods that have been described in the prior art to date of halogenated pyridine derivatives very frequently make use of methods that are not economically implementable from an industrial point of view and/or have other disadvantages.

In the case of lithium bases and magnesium bases in particular, disadvantages are the low chemical yields, performing at very low temperatures and the difficult regio- and chemoselectivity of the deprotonation due to the high reactivity of these reagents. Sometimes a transmetallation with zinc salts, such as zinc chloride for example, is necessary in order to carry out further selective reactions such as Negishi cross couplings as described, for example, in Organic Letters 2008 (10), p. 2497ff. The preparation is therefore very expensive (many salts are formed) and unsuitable for industrial scale commercial processes.

With regard to the disadvantages outlined above, there is an urgent need for a simplified, industrially and economically performable process for preparing halogenated pyridine derivatives, especially halogenated pyridine derivatives of the formula (II). The halogenated pyridine derivatives obtainable by this process sought are preferably to be obtained with good yield, high purity and in an economic manner.

SUMMARY

It has been found that, surprisingly, halogenated pyridine derivatives of the formula (II) can be prepared advantageously in a process using an organozinc base.

The present invention accordingly provides a process for preparing compounds of formula (II)

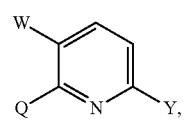

in which (configuration 1)
Q and W are each independently halogen, and
Y is halogen, $CO_2R^1$ or $NO_2$, where $R^1$ is $(C_1-C_6)$-alkyl or $(C_1-C_6)$-haloalkyl,
characterized in that, in a first process step a), a compound of the formula (I)

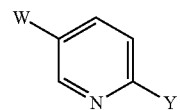

in which W and Y each have the definitions given above,
is reacted with an organozinc base of the structure $(NR^3R^4)$—Zn—$R^2$ or $(NR^3R^4)_2$—Zn in which $R^2$ is halogen or —O-pivaloyl and $R^3$ and $R^4$ together form a —$(CH_2)_4$—, —$(CH_2)_5$— or —$(CH_2)_2O(CH_2)_2$— group, where each of these groups may optionally be substituted by 1, 2, 3 or 4 $R^5$ radicals and $R^5$ is selected from the group consisting of methyl, ethyl, n-propyl and i-propyl, to give a compound of the formula (IIIa) or the formula (IIIb)

(IIIa)

(IIIb)

in which W, Y and $R^2$ each have the definitions given above, and this compound of the formula (IIIa) or (IIIb) is reacted in a second process step b) with a compound of the structure Q-X in which X is halogen and Q has the abovementioned definition to give the compound of the formula (II).

DETAILED DESCRIPTION OF A PREFERRED EMBODIMENT

The compound Q-X, as apparent from the definitions of Q and X, is an interhalogen compound, preferably elemental halogen.

Preferred and particularly preferred definitions of the Q, W, $R^1$, $R^2$, X and Y radicals included in the aforementioned formulae (I), (II), (IIIa) and (IIIb) of the process of the invention are elucidated hereinafter, with more specific description of the organozinc base further down, and so the preferred configurations of the base are specified at that point.

(Configuration 2)

Q and X have the same definition and are each preferably iodine or bromine,

W is preferably fluorine or chlorine, $R^2$ is preferably halogen, especially chlorine, bromine or iodine, and Y is preferably chlorine, bromine, $CO_2R^1$ or $NO_2$, where $R^1$ is $(C_1$-$C_4)$-alkyl.

(Configuration 3)

Q and X have the same definition and are each particularly preferably iodine,

W is particularly preferably fluorine, $R^2$ is particularly preferably chlorine, and Y is particularly preferably chlorine, bromine, $CO_2R^1$ or $NO_2$, where $R^1$ is methyl.

The radical definitions and elucidations given above apply both to the end products and intermediates and to the starting materials in a corresponding manner. These radical definitions can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being particularly preferred.

Advantageously, the halogenated pyridine derivatives of the formula (II) can be prepared by the process according to the invention with good yields and in high purity. Because of the very good functional group tolerance of zinc reagents, zinc bases are very attractive. Regio- and chemoselective metallations of pyridines in the presence of stoichiometric amounts of selective bases are possible, even at elevated temperatures, without aryne elimination taking place or sensitive functional groups being attacked. The zinc compound formed as intermediate can subsequently be scavenged with various electrophiles, as described by way of example in Organic Letters 2009 (11), p. 1837ff. These novel substituted pyridine derivatives can then be further reacted as valuable synthons.

In particular, the very good and unexpected highly selective regioselectivity of the metallation is advantageous, which occurs, particularly at relatively high temperatures (for example on heating to ca. 40 to 80° C., for example 60° C.), at the 6 position of the pyridine skeleton. Accordingly, the heating is then particularly advantageous if the regioselectivity is intended to be further improved. For example, a mixture of pyridines scavenged with iodine at positions 6 and 4 are formed at room temperature, whereas pyridines scavenged with iodine at position 6 are formed at relatively high temperature.

The process according to the invention can be elucidated by the following scheme (I):

Scheme (I)

In this scheme, Q, W, $R^1$, $R^2$, X and Y have the meanings given above. The compounds shown in brackets are the intermediate (formula IIIa or formula IIIb) which are reacted further to give the compound of the formula (II). Accordingly, the process according to the invention can be divided into the two process steps a) and b), step a) being the conversion of the compound of the formula (I) to the respective intermediate and step b) being the further conversion of the intermediate to the compound of the formula (II).

General Definitions

In the context of the present invention, the term halogen (Hal), unless defined otherwise, encompasses those elements selected from the group consisting of fluorine, chlorine, bromine and iodine.

The term "halides" in connection with the present invention describes compounds between halogens and elements of other groups of the Periodic Table, which can give rise to halide salts (ionic compounds (salts) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity), depending on the nature of the chemical bond. Particular preference is given in accordance with the invention to halide salts.

The term "pivaloyl" in the context of the present invention describes the deprotonated radical of pivalic acid (X) having the empirical formula $(CH_3)_3CCO_2H$.

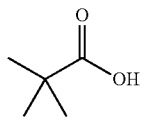
(X)

"O-pivaloyl" correspondingly means that the bond of the pivaloyl radical is via the deprotonated oxygen atom of the acid group.

Optionally substituted groups may be mono- or polysubstituted, where the substituents in the case of polysubstitutions may be the same or different.

Alkyl groups substituted by one or more halogen atoms (-Hal) are, for example, selected from trifluoromethyl ($CF_3$), difluoromethyl ($CHF_2$), $CF_3CH_2$, $ClCH_2$ or $CF_3CCl_2$.

Alkyl groups in the context of the present invention, unless defined otherwise, are linear, branched or cyclic saturated hydrocarbyl groups.

The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

The conversion of the compounds of the formula (I) to compounds of the formula (IIIa) or (IIIb) in the first process step (step a)) is effected in the presence of an organozinc base of the structure $(NR^3R^4)$—Zn—$R^2$ or $(NR^3R^4)_2$—Zn, in which (configuration B-1)

$R^2$ is as defined above (configuration 1) (and is therefore halogen or —O-pivaloyl), $R^3$ and $R^4$ together form a —$(CH_2)_4$—, —$(CH_2)_5$— or —$(CH_2)_2O(CH_2)_2$— group, where each of these groups may optionally be substituted by 1, 2, 3 or 4 $R^5$ radicals and $R^5$ is selected from the group consisting of methyl, ethyl, n-propyl and i-propyl.

It is preferable that (configuration B-2)

$R^2$ is as defined above as preferred (configuration 2) (and is therefore halogen, especially chlorine, bromine or iodine), $R^3$ and $R^4$ together form a —$(CH_2)_5$— group, where each of these groups may optionally be substituted by 1, 2, 3 or 4 $R^5$ radicals and $R^5$ is selected from the group consisting of methyl and ethyl.

It is particularly preferable that (configuration B-3)

$R^2$ is as defined above as particularly preferred (configuration 3) (and is therefore chlorine) and $R^3$ and $R^4$ together form a —$(CH_2)_5$— group substituted by 4 methyl groups.

The radical definitions given above can be combined with one another as desired, i.e. including combinations between the respective ranges of preference.

In a very particularly preferred configuration of the base according to the invention, the structural element $(NR^3R^4)$ is tetramethylpiperidine (TMP) of formula (IV).

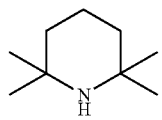
(IV)

Organozinc bases most preferred in accordance with the invention are accordingly characterized in that zinc is bound by TMP, especially in the form of zinc halide and most preferably in the form of zinc chloride. Bases of this kind have the following structure of the formula (V) (configuration B-4)

$(TMP)_xZnCl_{2-x}$, (V)

in which x is the number 1 or 2. Among these, preference is given in turn to bases with x=1 (configuration B-5) of formula (VI):

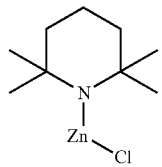
(VI)

In a further preferred embodiment of the process according to the invention, the organometallic base is present in conjunction with alkali metal or alkaline earth metal halides. This is especially true of bases of the formulae (V) and (VI). Particularly preferred alkali metal or alkaline earth metal halides of this kind are lithium chloride and magnesium chloride, very particular preference being given to lithium chloride. Organometallic bases that are very particularly preferred in accordance with the invention are accordingly TMP ZnCl.LiCl or $(TMP)_2$ Zn.2LiCl (configuration B-6). Most preferred is TMP ZnCl.LiCl (VII; configuration B-7).

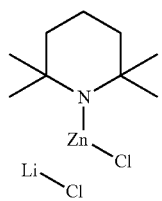
(VII)

Specific combinations of compounds of the formulae (I), (II) and (IIIa) or (IIIb) with bases according to the invention are cited in Table I below by way of example, these being employable in a process according to the invention. Since, in some configurations, the structural element $R^2$ is present both in the base according to the invention and in the compound of the formula (IIIa), the narrowest definition applies to $R^2$ in each case.

TABLE 1

| Number | Compounds of the formulae (I), (II) and (IIIa) or (IIIb) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |

Preferably, the organometallic base is used in the process according to the invention in a total amount of 0.5 to 5 equivalents, preferably of 0.8 to 2 equivalents, further preferably of 1 to 1.5 equivalents and more preferably of 1.0 to 1.2 equivalents, based on the compound of the formula (I). One advantage of the process according to the invention in this regard is that the organometallic base can be used in virtually stoichiometric amounts.

Depending on whether the structural element $(NR^3R^4)$ is present once or twice in the organozinc base used, intermediate compounds of the formula (IIIa) or of the formula (IIIb) are formed in process step a).

The conversion of the compounds of the formula (IIIa) or (IIIb) to compounds of the formula (II) in the second process step (step b)) is effected in the presence of a compound Q-X in which Q and X each have the definitions given above. Since both Q and X are halogen, the compound is an interhalogen compound. Q and X need not necessarily be the same halogen. For example, Q may be iodine or bromine and X may be chlorine, bromine or iodine. Preferably, the compound Q-X, however, is an elemental halogen, especially $F_2$, $Cl_2$, $Br_2$ or $I_2$. Particular preference is given to $I_2$ or $Br_2$, very particular preference to $I_2$.

Preferably, the compound Q-X is used in the process according to the invention in a total amount of 0.5 to 10.0 equivalents, preferably of 0.8 to 5 equivalents, further preferably of 1 to 2.5 equivalents and more preferably of 1.0 to 1.5 equivalents, based on the compound of the formula (I).

The inventive conversion of the compounds of the formula (I) to compounds of the formula (IIIa) or (IIIb) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the solvents mentioned above such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both process steps a) and b). Alternative configurations of the invention in which different solvents are used for process steps a) and b) are likewise possible, however, in which case the solvents are likewise preferably selected from the aforementioned solvents, and the respective solvents specified as being preferred, more preferred and most preferred are applicable to the respective process step a) or b).

The conversion in process step a) is generally conducted at a temperature between 0° C. and 80° C. and with increasing preference between 10° C. and 75° C., between 20° C. and 70° C., between 30° C. and 70° C., between 40° C. and 68° C., and most preferably between 50° C. and 65° C., for example at 60° C.

The conversion in process step b) is generally conducted at a temperature between 0° C. and 80° C. and with increasing preference between 10° C. and 70° C., between 15° C. and 60° C., between 20° C. and 50° C., between 20° C. and 40° C., and most preferably between 20° C. and 35° C., for example at room temperature or 25° C.

The reaction is typically conducted at standard pressure, but can also be conducted at elevated or reduced pressure.

The desired compounds of the formula (II) can be isolated, for example, by aqueous workup in the presence of saturated ammonium chloride or sodium thiosulphate solutions and/or subsequent chromatography. Such processes are known to those skilled in the art and also include crystallization from an organic solvent or solvent mixture.

A particularly preferred embodiment of the process according to the invention can be elucidated with reference to the following scheme (II):

Scheme II:

[Reaction scheme showing pyridine with W and Y substituents reacting with TMPZnCl·LiCl (1.0-1.2 equiv), THF to form intermediate [LiCl·ClZn-pyridine(W)(Y)], then with iodine (1.0-1.5 equiv), THF to form iodo-pyridine product with W and Y]

In this scheme, W and Y have the definitions given above. The compound shown in brackets represents the corresponding intermediate of the formula IIIa which is converted further to the product, a compound of the formula (II). Both reactions take place in THF as solvent. "Equiv" refers to the amount of equivalents of TMPZnCl LiCl or iodine ($I_2$) used.

The present invention further provides compounds of the formula (IIIa)

[Structure IIIa: pyridine with W at 3-position, $R^2$—Zn at 2-position, Y at 6-position]

in which
W is halogen,
Y is halogen, $CO_2R^1$ or $NO_2$, where $R^1$ is $(C_1-C_6)$-alkyl or $(C_1-C_6)$-haloalkyl, and
$R^2$ is halogen or —O-pivaloyl.

Preferred and particularly preferred definitions of the radicals included in the aforementioned formula (IIIa) are elucidated hereinafter.

W is preferably fluorine or chlorine,
Y is preferably chlorine, bromine, $CO_2R^1$ or $NO_2$, where $R^1$ is $(C_1-C_4)$-alkyl, and
$R^2$ is preferably halogen, especially chlorine, bromine and iodine.

W is particularly preferably fluorine,
Y is particularly preferably chlorine, bromine, $CO_2R^1$ or $NO_2$, where $R^1$ is methyl, and
$R^2$ is particularly preferably chlorine.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Among the compounds of the formula (IIIa), the following compounds are especially preferred, in which the respective compound can be present alone or as a lithium chloride complex:

IIIa-1

[Two structures: 3-fluoro-6-chloropyridine with ClZn at 2-position; same structure with LiCl]

Chloro(6-chloro-3-fluoropyridin-2-yl)zinc

Chloro(6-chloro-3-fluoropyridin-2-yl)zinc lithium chloride complex

IIIa-2

[Two structures: 3-fluoro-6-bromopyridine with ClZn at 2-position; same with LiCl]

6-Bromo-3-fluoropyridin-2-yl)(chloro)zinc

6-Bromo-3-fluoropyridin-2-yl)(chloro)zinc lithium chloride complex)

IIIa-3

[Two structures: 3-fluoro-6-(methoxycarbonyl)pyridine with ClZn at 2-position; same with LiCl]

Chloro[3-fluoro-6-(methoxycarbonyl)pyridin-2-yl]zinc

Chloro[3-fluoro-6-(methoxycarbonyl)pyridin-2-yl]zinc lithium chloride complex)

IIIa-4

[Two structures: 3-fluoro-6-nitropyridine with ClZn at 2-position; same with LiCl]

Chloro(3-fluoro-6-nitropyridin-2-yl)zinc

Chloro(3-fluoro-6-nitropyridin-2-yl)zinc lithium chloride complex

The present invention further provides compounds of the formula (IIIb)

[Structure IIIb: two pyridine rings connected through Zn, each with W and Y substituents]

in which
W is halogen, and
Y is halogen, $CO_2R^1$ or $NO_2$, where $R^1$ is $(C_1-C_6)$-alkyl or $(C_1-C_6)$-haloalkyl.

Preferred and particularly preferred definitions of the radicals included in the aforementioned formula (IIIb) are elucidated hereinafter.

W is preferably fluorine or chlorine, and
Y is preferably chlorine, bromine, $CO_2R^1$ or $NO_2$, where $R^1$ is $(C_1-C_4)$-alkyl.

W is particularly preferably fluorine, and
Y is particularly preferably chlorine, bromine, $CO_2R^1$ or $NO_2$, where $R^1$ is methyl.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

The present invention further provides compounds of the formula (II)

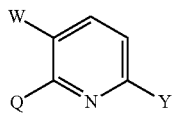

(II)

in which

Q and W are each independently halogen, wherein in particular Q is iodine, and

Y is halogen, $CO_2R^1$ or $NO_2$, where $R^1$ is $(C_1-C_6)$-alkyl or $(C_1-C_6)$-haloalkyl.

Preferred and particularly preferred definitions of the radicals included in the aforementioned formula (II) are elucidated hereinafter.

Q is preferably iodine or bromine, especially iodine,

W is preferably fluorine or chlorine, and

Y is preferably chlorine, bromine, $CO_2R^1$ or $NO_2$, where $R^1$ is $(C_1-C_4)$-alkyl.

Q is particularly preferably iodine,

W is particularly preferably fluorine, and

Y is particularly preferably chlorine, bromine, $CO_2R^1$ or $NO_2$, where $R^1$ is methyl.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Among the compounds of the formula (II), the following compounds are especially preferred:

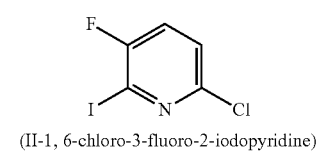

(II-1, 6-chloro-3-fluoro-2-iodopyridine)

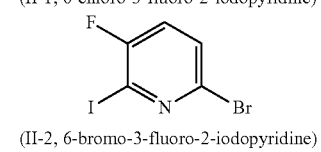

(II-2, 6-bromo-3-fluoro-2-iodopyridine)

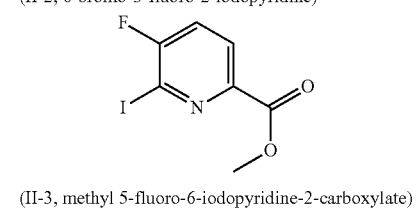

(II-3, methyl 5-fluoro-6-iodopyridine-2-carboxylate)

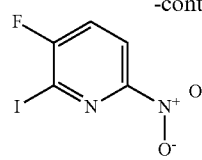

(II-4, 3-fluoro-2-iodo-6-nitropyridine)

From these compounds of the formulae (II-1) to (II-4) arise the accompanying reactants (I-1 to I-4) of the formula (I) of the process according to the invention, which in each case are especially preferred compounds of the formula (I).

The present invention is elucidated in more detail by the examples which follow, although the examples should not be interpreted in such a manner that they restrict the invention.

EXAMPLE 1

Synthesis of 6-chloro-3-fluoro-2-iodopyridine

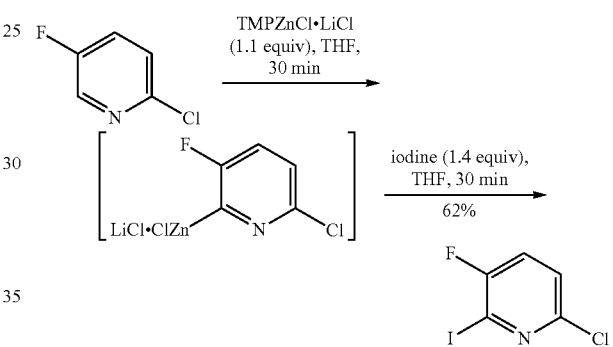

To 2-chloro-5-fluoropyridine (132 mg, 1.0 mmol), dissolved in THF (2 ml), is added TMPZnCl.LiCl (1.31M in THF, 0.84 ml, 1.1 mmol) at 60° C. under argon; this reaction solution is stirred for 30 min. Subsequently, iodine (355 mg in 4 ml of THF) is added at 25° C. and the solution is stirred for a further 30 min. After customary workup by addition of saturated ammonium chloride and sodium thiosulphate solutions, the reaction mixture is extracted with ethyl acetate, and the combined organic phases are dried over $Na_2SO_4$ and concentrated in the membrane pump vacuum. After purification by column chromatography (ethyl acetate/cyclohexane), 6-chloro-3-fluoro-2-iodopyridine (158 mg, 62%) is obtained as a yellow solid. HPLC-MS: log P=2.53; mass (m/z): no ionization; 1H-NMR (D6-DMSO): δ 7.80 (m, 1H), 7.61 (m, 1H).

EXAMPLE 2

Synthesis of methyl 5-fluoro-6-iodopyridine-2-carboxylate

To methyl 5-fluoropyridine-2-carboxylate (155 mg, 1.0 mmol), dissolved in THF (2 ml), is added TMPZnCl.LiCl (1.31M in THF, 0.84 ml, 1.1 mmol) at 60° C. under argon; this reaction solution is stirred for 30 min. Subsequently, iodine (355 mg in 4 ml of THF) is added at 25° C. and the solution is stirred for a further 30 min. After customary workup and purification by column chromatography (ethyl acetate/cyclohexane), methyl 5-fluoro-6-iodopyridine-2- carboxylate (197 mg, 70%) is obtained as a yellow solid. HPLC-MS: log P=1.85; mass (m/z): 281.9; 1H-NMR (D6-DMSO): δ 8.10 (m, 1H), 7.86 (m, 1H), 3.89 (s, 3H).

EXAMPLE 3

Synthesis of 6-bromo-3-fluoro-2-iodopyridine

To 2-bromo-5-fluoropyridine (880 mg, 5.0 mmol), dissolved in THF (5 ml), is added TMPZnCl.LiCl (1.31M in THF, 4.2 ml, 5.5 mmol) at 60° C. under argon; this reaction solution is stirred for 30 min. Subsequently, iodine (1.78 g in 4 ml of THF) is added at 25° C. and the solution is stirred for a further 30 min. After customary workup by addition of saturated ammonium chloride and sodium thiosulphate solutions, the reaction mixture is extracted with ethyl acetate, and the combined organic phases are dried over $Na_2SO_4$ and concentrated in the membrane pump vacuum. After purification by column chromatography (ethyl acetate/cyclohexane), 6-bromo-3-fluoro-2-iodopyridine (1.31 g, 87%) is obtained as a yellow solid. HPLC-MS: log P=2.67; mass (m/z): no ionization; 1H-NMR (D6-DMSO): δ 7.72 (m, 2H).

The invention claimed is:

1. A process for preparing a compound of formula (II)

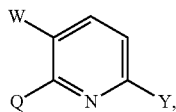

(II)

wherein
Q and W are each independently halogen, and
Y is halogen, $CO_2R^1$ or $NO_2$, where $R^1$ is $(C_1$-$C_6)$-alkyl or $(C_1$-$C_6)$-haloalkyl,
wherein, in a first process step a), a compound of formula (I)

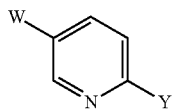

(I)

wherein W and Y each have the definitions given above, is reacted with an organozinc base of structure $(NR^3R^4)$—Zn—$R^2$ or $(NR^3R^4)_2$—Zn wherein
$R^2$ is halogen or O-pivaloyl and
$R^3$ and $R^4$ together form a —$(CH_2)_4$—, —$(CH_2)_5$— or —$(CH_2)_2O(CH_2)_2$— group, where each of these groups may optionally be substituted by 1, 2, 3 or 4 $R^5$ radicals and $R^5$ is selected from the group consisting of methyl, ethyl, n-propyl and i-propyl,
to give a compound of formula (IIIa) or formula (IIIb)

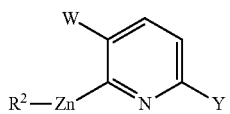

(IIIa)

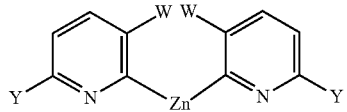

(IIIb)

wherein W, Y and $R^2$ each have the definitions given above,
wherein the step a) is conducted at a temperature between 30° C. and 80° C.,
and this compound of formula (IIIa) or (IIIb) is reacted in a second process step b) with a compound of the structure Q-X wherein X is halogen and Q has the abovementioned definition to give the compound of formula (II).

2. The process according to claim 1, wherein
Q and X have the same definition and are each iodine or bromine,
W is fluorine or chlorine,
$R^2$ is halogen, and
Y is chlorine, bromine, $CO_2R^1$ or $NO_2$, where $R^1$ is $(C_1$-$C_4)$-alkyl.

3. The process according to claim 1, wherein
$R^3$ and $R^4$ together form a —$(CH_2)_5$— group, where each of these groups may optionally be substituted by 1, 2, 3 or 4 $R^5$ radicals, and
$R^5$ is selected from the group consisting of methyl and ethyl.

4. The process according to claim 1, wherein
Q and X have the same definition and are each iodine,
W is fluorine,
$R^2$ is chlorine, and
Y is chlorine, bromine, $CO_2R^1$ or $NO_2$, where $R^1$ is methyl.

5. The process according to claim 1, wherein
$R^3$ and $R^4$ together form a —$(CH_2)_5$— group substituted by 4 methyl groups.

6. The process according to claim 1, wherein the organozinc base is a compound of formula (V)

$$(TMP)_xZnCl_{2-x},$$  (V)

wherein x is the number 1 or 2.

7. The process according to claim 1, wherein the organozinc base is present in conjunction with an alkali metal halide or alkaline earth metal halide.

8. The process according to claim 1, wherein the organozinc base is used in a total amount of 0.5 to 5 equivalents, based on the compound of formula (I).

9. The process according to claim 1, wherein the compound Q-X is an elemental halogen, optionally $F_2$, $Cl_2$, $Br_2$ or $I_2$.

10. The process according to claim 1, wherein the compound Q-X is used in a total amount of 0.5 to 10.0 equivalents, based on the compound of formula (I).

11. The process according to claim 1, that is conducted in the presence of a solvent selected from the group consisting of tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbon, aromatic hydrocarbon, chlorohydrocarbon, tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, 1,2-dichlorobenzene, chlorotoluene, trichlorobenzene; 4-methoxybenzene, fluorinated aliphatic, fluorinated aromatic, trichlorotrifluoroethane, benzotrifluoride and 4-chlorobenzotrifluoride, or a mixture of at least two of these solvents with one another.

12. The process according to claim 11, wherein the solvent is THF or N,N-dimethylformamide (DMF).

13. The process according to claim 1, wherein step b) is conducted at a temperature between 0° C. and 80° C.

14. A compound of formula (IIIa)

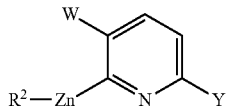

(III)

wherein
W is fluorine,
Y is halogen, C(O)$_2$R$^1$ or N(O)$_2$, where R$^1$ is (C$_1$-C$_6$)-alkyl or (C$_1$-C$_6$)-haloalkyl, and
R$^2$ is halogen or O-pivaloyl.

15. A compound of formula (IIIb)

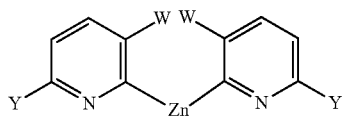

(IIIb)

wherein
W is fluorine, and
Y is halogen, CO$_2$R$^1$ or NO$_2$, where R$^1$ is (C$_1$-C$_6$)-alkyl or (C$_1$-C$_6$)-haloalkyl.

16. A compound of formula (II)

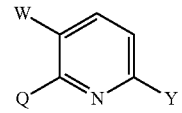

(II)

wherein
Q is iodine,
W is fluorine, and
Y is Br, C(O)$_2$R$^1$ or N(O)$_2$, where R$^1$ is (C$_1$-C$_6$)-alkyl or (C$_1$-C$_6$)-haloalkyl.

17. The process according to claim 2, wherein R$^2$ is chlorine, bromine or iodine.

18. The process according to claim 7, wherein the organozinc base is present in conjunction with lithium chloride or magnesium chloride.

19. The process according to claim 4, wherein Y is bromine.

* * * * *